US010219770B2

(12) United States Patent
Enomoto et al.

(10) Patent No.: US 10,219,770 B2
(45) Date of Patent: Mar. 5, 2019

(54) RADIOGRAPHIC IMAGE PROCESSING DEVICE, METHOD, AND PROGRAM

(71) Applicant: FUJIFILM Corporation, Tokyo (JP)

(72) Inventors: Jun Enomoto, Ashigarakami-gun (JP); Takashi Tajima, Ashigarakami-gun (JP); Takeshi Koishi, Ashigarakami-gun (JP); Haruyasu Nakatsugawa, Ashigarakami-gun (JP); Hirofumi Sawada, Ashigarakami-gun (JP); Daiki Harada, Ashigarakami-gun (JP); Takahiro Kawamura, Ashigarakami-gun (JP); Satoshi Naito, Ashigarakami-gun (JP); Hideki Yamagishi, Ashigarakami-gun (JP); Noriaki Ida, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 367 days.

(21) Appl. No.: 15/141,193

(22) Filed: Apr. 28, 2016

(65) Prior Publication Data
US 2016/0235385 A1 Aug. 18, 2016

Related U.S. Application Data

(63) Continuation of application No. PCT/JP2014/005574, filed on Nov. 5, 2014.

(30) Foreign Application Priority Data

Nov. 6, 2013 (JP) ................................ 2013-229944

(51) Int. Cl.
*A61B 6/00* (2006.01)

(52) U.S. Cl.
CPC ............ *A61B 6/5282* (2013.01); *A61B 6/461* (2013.01); *A61B 6/463* (2013.01)

(58) Field of Classification Search
CPC ........ A61B 6/461; A61B 6/463; A61B 6/5282
See application file for complete search history.

(56) References Cited

U.S. PATENT DOCUMENTS

| 5,960,058 A | 9/1999 | Baba et al. |
| 8,064,676 B2 | 11/2011 | Li et al. |

(Continued)

FOREIGN PATENT DOCUMENTS

| JP | 02-244881 A | 9/1990 |
| JP | 06-014911 A | 1/1994 |

(Continued)

OTHER PUBLICATIONS

Christiaan Fivez, et al. "Multi-Resolution Contrast Amplification in Digital Radiography with Compensation for Scattered Radiation", IEEE, 1996, pp. 339-342, vol. 1.

(Continued)

*Primary Examiner* — Chih-Cheng Kao
(74) *Attorney, Agent, or Firm* — Sughrue Mion, PLLC

(57) ABSTRACT

A radiographic image captured by irradiating a subject with radiation is acquired. A scattered radiation removal unit removes a scattered component from the radiographic image using at least imaging conditions. A correction information acquisition unit acquires correction information for correcting the degree of removal of the scattered component and changes the imaging conditions on the basis of the correction information. The scattered radiation removal unit performs a process of removing the scattered component from the radiographic image on the basis of the changed imaging conditions.

8 Claims, 11 Drawing Sheets

(56) References Cited

U.S. PATENT DOCUMENTS

| | | | | |
|---|---|---|---|---|
| 2002/0141541 | A1* | 10/2002 | Darboux | A61B 6/483 378/210 |
| 2005/0078799 | A1* | 4/2005 | Ancelin | A61B 6/502 378/154 |
| 2009/0022273 | A1* | 1/2009 | Kashiwagi | A61B 6/502 378/37 |
| 2010/0215243 | A1* | 8/2010 | Ohno | A61B 6/06 382/132 |
| 2013/0202086 | A1 | 8/2013 | Tsuji | |
| 2015/0297167 | A1 | 10/2015 | Tsuji | |
| 2016/0267630 | A1* | 9/2016 | Naito | A61B 6/5282 |
| 2016/0349195 | A1* | 12/2016 | Inoue | A61B 6/5282 |
| 2017/0296133 | A1* | 10/2017 | Katsumata | A61B 6/5282 |

FOREIGN PATENT DOCUMENTS

| | | |
|---|---|---|
| JP | 09-149895 A | 6/1997 |
| JP | 2008-011894 A | 1/2008 |
| JP | 2008-136602 A | 6/2008 |
| JP | 2010-240028 A | 10/2010 |
| JP | 2013-176544 A | 9/2013 |

OTHER PUBLICATIONS

Dinko E. González Trotter, et al., "Thickness-dependent Scatter Correction Algorithm for Digital Mammography", Proc. SPIE, May 2002, pp. 469-478, vol. 4682.

John M. Boone, et al., "An analytical model of the scattered radiation distribution in diagnostic radiology", Med. Phys., Sep./Oct. 1988, pp. 721-726, vol. 15, No. 5.

International Search Report for PCT/JP2014/005574 dated Mar. 3, 2015 [PCT/ISA/210].

Written Opinion for PCT/JP2014/005574 dated Mar. 3, 2015 [PCT/ISA/237].

\* cited by examiner

| IMAGING PROCEDURE | IMAGING CONDITIONS | | |
|---|---|---|---|
| | TUBE VOLTAGE | mAs VALUE | |
| | | mA | mSec |
| POSTEROANTERIOR CHEST RADIOGRAPHY | 120kV | 1 | 2 |
| LATERAL CHEST RADIOGRAPHY | 120kV | 1 | 1 |
| POSTEROANTERIOR ABDOMEN RADIOGRAPHY | 80kV | 1 | 1 |
| EXTREMITY RADIOGRAPHY | 80kV | 1 | 2 |
| | | | |

FIG. 3 — LUT1

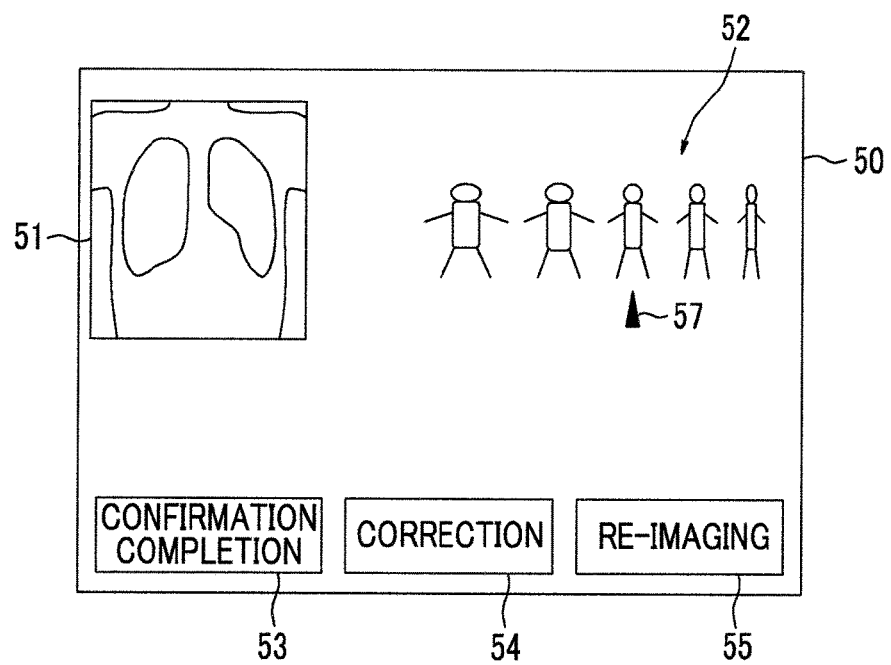

RADIOGRAPHIC IMAGE PROCESSING DEVICE, METHOD, AND PROGRAM

CROSS-REFERENCE TO RELATED APPLICATIONS

This application is a Continuation of PCT International Application No. PCT/JP2014/005574 filed on Nov. 5, 2014, which claims priority under 35 U.S.C. § 119(a) to Japanese Patent Application No. 2013-229944 filed on Nov. 6, 2013. Each of the above applications is hereby expressly incorporated by reference, in its entirety, into the present application.

BACKGROUND OF THE INVENTION

1. Field of the Invention

The present invention relates to a radiographic image processing device and method which performs image processing including a scattered radiation removal process for a radiographic image and a program which causes a computer to perform a radiographic image processing method.

2. Description of the Related Art

In the related art, during the capture of a radiographic image of a subject using radiation that is transmitted through the subject, particularly, if the thickness of the subject is large, the radiation is scattered in the subject and the scattered radiation (hereinafter, also referred to as a scattered ray) causes a reduction in the contrast of the acquired radiographic image. For this reason, in some cases, when a radiographic image is captured, a scattered radiation removal grid (hereinafter, simply referred to as a grid) is provided between a subject and a radiation detector which detects radiation and acquires a radiographic image such that the scattered radiation is not emitted to the radiation detector. When imaging is performed using the grid, radiation which is scattered by the subject is less likely to be emitted to the radiation detector. Therefore, the use of the grid makes it possible to improve the contrast of the radiographic image.

In contrast, when imaging is performed using the grid, a subject image and a fine stripe pattern (moire) corresponding to the grid are included in the radiographic image, which makes it difficult to see the image. For this reason, a process is known which removes a stripe pattern caused by the grid from a radiographic image.

The grid has a structure in which radiopaque lead and a radiolucent interspace material, such as aluminum or fiber, are alternately arranged at a fine grid density of, for example, about 4.0 lines/mm. Therefore, the grid is weighty. For this reason, in portable radiography which is performed in, for example, a hospital room using a visiting car equipped with an imaging device, the grid needs to be provided between a lying patent and a radiation detector, which causes an increase in the burden of an arrangement operation on a radiographer and an increase in strain on the patient during imaging. Further, in the case of a convergence-type grid, density unevenness is likely to occur in the radiographic image due to the oblique incidence of radiation. In addition, a subject image and a fine stripe pattern (moire) corresponding to the pitch of the grid are recorded on the radiographic image, which makes it difficult to see the radiographic image.

For this reason, a process has been proposed which captures a radiographic image, without using a grid, and gives an image quality improvement effect, which can be obtained by removing scattered radiation using a grid, to the radiation image through image processing on the basis of imaging conditions (see U.S. Pat. No. 8,064,676B, JP1994-014911A (JP-H06-014911A), and C. Fivez et al., "Multi-resolution contrast amplification in digital radiography with compensation for scattered radiation", 1996, IEEE, pp. 339-342). The methods described in U.S. Pat. No. 8,064,676B and C. Fivez et al., "Multi-resolution contrast amplification in digital radiography with compensation for scattered radiation", 1996, IEEE, pp. 339-342 decompose a radiographic image into a plurality of frequency components, perform a scattered radiation removal process of controlling contrast or latitude for a low-frequency component which is regarded as a scattered radiation component, and combine the processed frequency components to acquire a radiographic image from which the scattered radiation component has been removed. In the method described in U.S. Pat. No. 8,064,676B, the scattered radiation removal process is performed by multiplying a low-frequency component by a gain corresponding to the hierarchy of the low-frequency component and the pixel value of the low-frequency component. Here, the gain is less than 1. The gain has a smaller value in a lower frequency band and is reduced as the pixel value increases. The method described in C. Fivez et al., "Multi-resolution contrast amplification in digital radiography with compensation for scattered radiation", 1996, IEEE, pp. 339-342 uses a table for converting a low-frequency component according to the pixel value thereof. In the method, lower frequency bands are increasingly reduced in a geometric progression manner.

According to the methods described in U.S. Pat. No. 8,064,676B, JP1994-014911A (JP-H06-014911A), and C. Fivez et al., "Multi-resolution contrast amplification in digital radiography with compensation for scattered radiation", 1996, IEEE, pp. 339-342, since no grid is required during imaging, it is possible to reduce strain on a patient during imaging and to prevent the deterioration of image quality due to density unevenness and moire.

In addition, the following method is known: when a radiographic image of a subject is captured using radiation that is transmitted through the subject, the radiation is more likely to be scattered in the subject and radiation transmittance becomes lower as the thickness of the subject increases, which results in a variation in the quality of the acquired radiographic image. For this reason, a technique has been proposed which roughly estimates the thickness of a subject, on the basis of various kinds of information, such as imaging conditions, a signal value of a radiographic image, the width of the histogram of the signal value of the radiographic image, and the length of the subject in a predetermined direction in the radiographic image and changes the conditions of imaging processing, such as a scattered radiation removal process for the captured radiographic image, or imaging conditions applied to capture a radiographic image, on the basis of the estimated thickness of the subject.

For example, JP1990-244881A (JP-H02-244881A) discloses a method which measures pixel values of a radiograph image of a simulated subject with a known thickness that is captured under known imaging conditions, prepares a correspondence table in which a body thickness is associated with the pixel value in advance, roughly estimates a body thickness distribution on the basis of the pixel value of the radiographic image with reference to the correspondence table, estimates a scattered component of the radiographic image corresponding to the body thickness distribution of the radiographic image, and subtracts the scattered component from the radiographic image to acquire a processed image.

In addition, Trotter et al., "Thickness-dependent Scatter Correction Algorithm for Digital Mammography", Proc. SPIE, Vol. 4682, May 2002, pp. 469-478 discloses a method which estimates a scattered component of a radiographic image on the basis of a human body thickness distribution and removes the scattered component. The method disclosed in Trotter et al., "Thickness-dependent Scatter Correction Algorithm for Digital Mammography", Proc. SPIE, Vol. 4682, May 2002, pp. 469-478 applies a predetermined function to an input radiographic image on the basis of the body thickness distribution estimated from the pixel value of the radiographic image to generate an estimated scattered radiation image, which is obtained by estimating the image of scattered radiation included in the radiographic image, and subtracts the estimated scattered radiation image from the radiographic image to generate an estimated primary radiation image which is obtained by estimating a primary radiation image from the input radiographic image. In addition, the method repeatedly performs the process which applies a predetermined function to the generated estimated primary radiation image to generate the estimated scattered radiation image and subtracts the estimated scattered radiation image from the radiographic image to generate the estimated primary radiation image until the estimated scattered radiation image is converged under predetermined convergence conditions, calculates a converged estimated scattered radiation image, and subtracts the estimated scattered radiation image from the radiographic image to finally obtain a processed image from which the scattered component has been removed. In addition, C. Fivez et al., "Multi-resolution contrast amplification in digital radiography with compensation for scattered radiation", 1996, IEEE, pp. 339-342 discloses a method which adjusts a predetermined function for estimating the image of scattered radiation included in the radiographic image according to the body thickness.

In contrast, in a general radiography system, when the imaging procedure (for example, a part of which the image is to be captured, an imaging direction (front or side), the purpose of radiologic interpretations, imaging conditions, the target of a radiation source, and the type of filter) of a patient, who is a subject of which the image is to be captured, is input to the system, default imaging conditions (for example, a tube voltage, an mAs value (that is, tube current×exposure time) which is a tube current-time product), and a source-image receptor distance (SID)) are set in the radiation source. When there are no problems in the default imaging conditions, the system captures an image using the imaging conditions to acquire a desired radiographic image. Therefore, a table in which default imaging conditions are associated with various imaging procedures is stored in the system. During imaging, imaging conditions corresponding to a designated imaging procedure are set and imaging is performed. In addition, the imaging procedure is stored together with a radiographic image. Therefore, in a case in which, for example, imaging processing is performed for the radiographic image after imaging, it is possible to acquire the imaging conditions when the radiographic image is acquired, with reference to information about the imaging procedure which is stored together with the radiographic image.

SUMMARY OF THE INVENTION

In order to remove the influence of scattered radiation from a radiographic image, a method may be used which acquires virtual grid characteristics, which are the characteristics of a virtual grid that is assumed to be used to remove scattered radiation when the radiographic image is captured, and performs a scattered radiation removal process for the radiographic image on the basis of the virtual grid characteristics. In a case in which the scattered radiation removal process is performed, it is possible to acquire the virtual grid characteristics on the basis of imaging conditions when the radiographic image is acquired and to perform the scattered radiation removal process. For example, it is possible to acquire a part of which the image is to be captured and the characteristics of the virtual grid that is assumed to be used for the part, using the imaging conditions corresponding to an imaging procedure used during imaging, and to perform the scattered radiation removal process on the basis of the characteristics of the virtual grid and the imaging conditions during imaging.

However, in some cases, the imaging conditions which have been set according to the imaging procedure are corrected according to the body type of the subject. For example, in some cases, the imaging conditions are corrected such that a tube voltage and/or an mAs value increases for a fat subject and the tube voltage and/or the mAs value decreases for a thin subject. Here, in general, the imaging conditions which have been actually used are not acquired in the stage of image processing which is performed after imaging. Particularly, in a case in which an imaging device and an image processing device are produced by different manufacturers or in a case in which portable radiography is performed in a hospital room using a visiting car, in many cases, it is difficult to acquire the imaging conditions in the subsequent stage.

In this case, the imaging conditions used in the scattered radiation removal process are different from the actual imaging conditions used for imaging. Therefore, it is difficult to remove a scattered component with high accuracy. As a result, it is difficult to obtain a radiographic image with desired image quality. In this case, the following method may be considered: the actual imaging conditions are noted and the actual imaging conditions are input to the system during the scattered radiation removal process. However, this operation of the operator is complicated and the note is likely to be lost.

The invention has been made in view of the above-mentioned problems and an object of the invention is to provide a technique which can remove scattered radiation included in a radiographic image with high accuracy and can acquire a high-quality radiographic image.

According to the invention, there is provided a radiographic image processing device comprising: image acquisition means for acquiring a radiographic image which is captured by irradiating a subject with radiation; scattered radiation removal processing means for performing a process of removing a scattered component included in the radiation that is transmitted through the subject during imaging from the radiographic image, using at least imaging conditions; and correction information acquisition means for acquiring correction information for correcting a degree of removal of the scattered component and changing the imaging conditions on the basis of the correction information, in response to an instruction to correct the radiographic image subjected to the scattered radiation removal process. The scattered radiation removal means performs the process of removing the scattered component from the radiographic image on the basis of the changed imaging conditions.

Here, when a radiographic image is captured, imaging conditions corresponding to an imaging procedure are set.

The "imaging conditions" mean, for example, imaging conditions which are set in advance according to the procedure.

In the radiographic image processing device according to the invention, the correction information may be information related to a body type of the subject.

The "information related to the body type" is information indicating the body type of the subject and can be, for example, information, such as a fat body type and a thin body type.

The radiographic image processing device according to the invention may further comprise body thickness distribution estimation means for estimating a body thickness distribution of the subject on the basis of the radiographic image and the imaging conditions. The correction information acquisition means may acquire information related to the body thickness distribution as the correction information and change the imaging conditions on the basis of the correction information, in response to the correction instruction. The body thickness distribution estimation means may estimate the body thickness distribution on the basis of the changed imaging conditions.

In this case, the scattered radiation removal processing means may perform the process of removing the scattered component on the basis of the changed imaging conditions and the body thickness distribution.

In the radiographic image processing device according to the invention, the correction information acquisition means may acquire the information related to the body type of the subject on the basis of the body thickness distribution, display the information related to the body type, receive an input of the correction information, and acquire the correction information.

In this case, the correction information acquisition means may detect an implant region from the radiographic image and acquire the information related to the body type on the basis of the body thickness distribution in a region other than the implant region in the radiographic image.

The "implant region" is a region corresponding to an implant, such as metal or silicon, which is inserted into the subject in the radiographic image. Since the brightness of the implant region is higher than that of the tissues of the subject, it is possible to extract the implant region from the radiographic image, using threshold processing.

According to the invention, there is provided a radiographic image processing method comprising: acquiring a radiographic image which is captured by irradiating a subject with radiation; performing a process of removing a scattered component included in the radiation that is transmitted through the subject during imaging from the radiographic image, using at least imaging conditions; acquiring correction information for correcting a degree of removal of the scattered component and changing the imaging conditions on the basis of the correction information, in response to an instruction to correct the radiographic image subjected to the scattered radiation removal process; and performing the process of removing the scattered component from the radiographic image on the basis of the changed imaging conditions.

According to the invention, there is provided a program that causes a computer to perform the radiographic image processing method according to the invention.

According to the invention, a scattered component included in radiation that is transmitted through a subject during imaging is removed from a radiographic image, using at least imaging conditions, and correction information is acquired in response to an instruction to correct the radiographic image subjected to a scattered radiation removal process. Then, the imaging conditions are changed on the basis of the correction information and the scattered component is removed from the radiographic image on the basis of the changed imaging conditions. Therefore, it is possible to appropriately remove the scattered component on the basis of the correction information. As a result, it is possible to acquire a high-quality radiographic image.

A body thickness distribution of the subject is estimated. The information of the body thickness distribution is acquired as the correction information and the imaging conditions are changed on the basis of the correction information, in response to the correction instruction. The body thickness distribution is estimated on the basis of the changed imaging conditions. Therefore, it is possible to appropriately estimate the body thickness distribution.

In this case, a process of removing the scattered component is performed on the basis of the changed imaging conditions and the body thickness distribution. Therefore, it is possible to appropriately remove the scattered component on the basis of the estimated body thickness distribution. As a result, it is possible to acquire a high-quality radiographic image.

In addition, information related to the body type of the subject is acquired on the basis of the body thickness distribution and is then displayed. Then, an input of the correction information is received. Therefore, it is easy to input the correction information and it is possible to reduce a burden on the operator.

In this case, the information related to the body type is acquired on the basis of the body thickness distribution of a region other than an implant region in the radiographic image. Therefore, it is possible to accurately acquire the information related to the body type.

BRIEF DESCRIPTION OF THE DRAWINGS

FIG. 3 is a diagram illustrating a table in which various imaging procedures and imaging conditions are associated with each other.

FIG. 6 is a diagram illustrating an example of a confirmation screen.

FIG. 7 is a diagram illustrating a table in which various kinds of correction information and imaging conditions are associated with each other.

DESCRIPTION OF THE PREFERRED EMBODIMENTS

Figure 1:
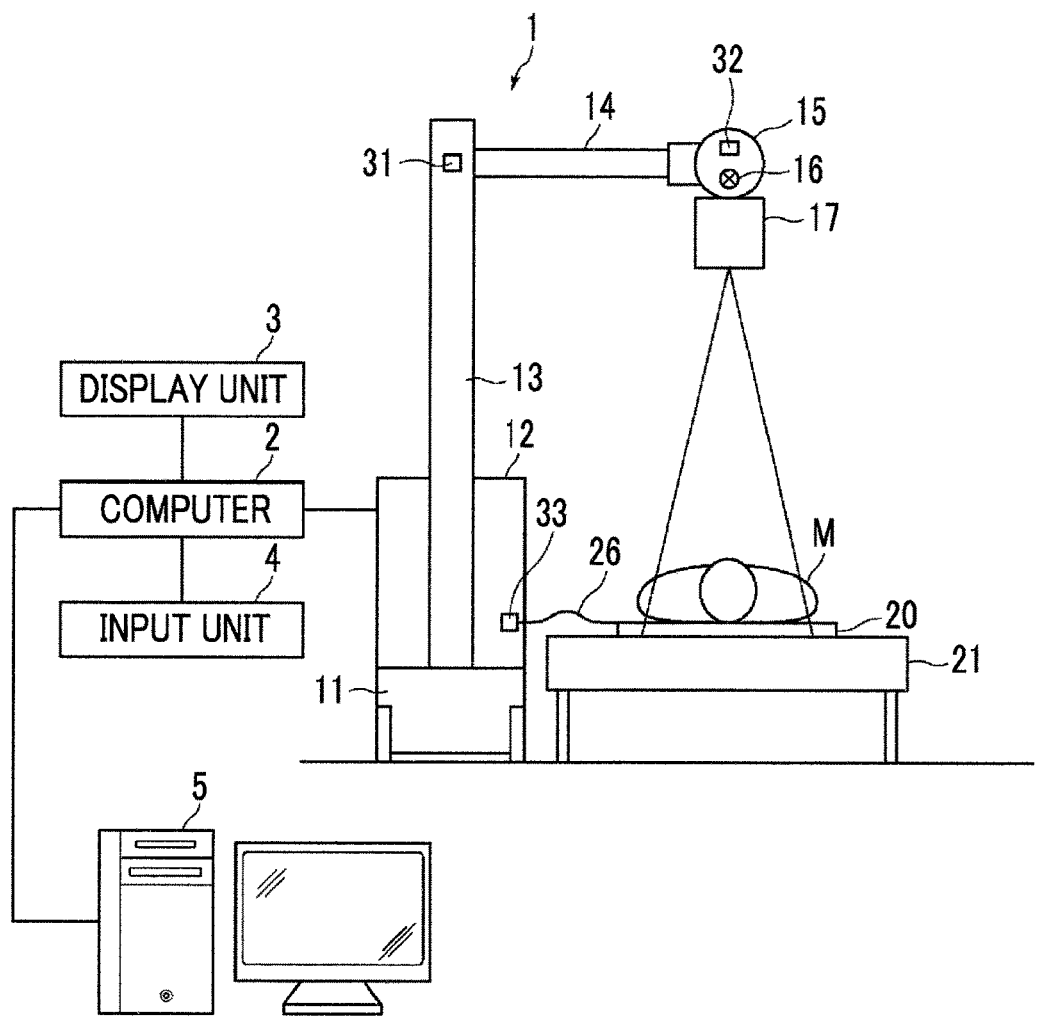
FIG. 1 is a block diagram schematically illustrating the structure of a radiography system to which a radiographic image processing device according to a first embodiment of the invention is applied.

Hereinafter, embodiments of the invention will be described with reference to the drawings. FIG. 1 is a block diagram schematically illustrating the structure of a radiography system to which a radiographic image processing device according to a first embodiment of the invention is applied. As illustrated in FIG. 1, a radiography system 1 according to this embodiment includes a movable imaging device. In the radiography system 1, a control device 12 which controls the radiography system 1 is provided on a movable carriage 11. The control device 12 includes a computer 2, and a display unit 3 and an input unit 4 which are connected to the computer 2. In FIG. 1, the computer 2, the display unit 3, and the input unit 4 are connected to the outside of the control device 12 for convenience of explanation. However, the computer 2, the display unit 3, and the input unit 4 are provided in the control device 12. In addition, the radiography system 1 is connected to a center console PC 5 which is provided in a hospital by the computer 2 through a network.

A support 13 is attached to the movable carriage 11 so as to pivot on the carriage 11 in the vertical direction. A radiation source supporting arm 14 which is movable in the vertical direction along the support 13 and in a direction perpendicular to the length direction of the support 13 is provided in the support 13. An arm controller 31 which is incorporated into the support 13 controls the rotation of the radiation source supporting arm 14 and the movement of the radiation source supporting arm 14 in the vertical direction and the direction perpendicular to the support 13. A radiation emitting unit 15 is attached to the leading end of the radiation source supporting arm 14. The radiation emitting unit 15 includes a radiation source 16 and a radiation source controller 32. In addition, a collimator 17 for setting the irradiation range of radiation is attached to a lower part of the radiation emitting unit 15.

An irradiation field lamp (not illustrated) is provided in the collimator 17. The irradiation field lamp is turned on to set the irradiation range of radiation for a subject when positioning is performed to prepare for imaging.

The radiation source controller 32 controls the time when radiation is emitted from the radiation source 16 and the imaging conditions (for example, a tube current and an mAs value) of the radiation source 16.

The mobile radiography system 1 is generally kept at a predetermined position in the hospital. When a radiographic image of a subject M who lies on a bed 21 needs to be captured, the radiography system 1 is moved into the hospital and is used to capture the radiographic image of the subject M on the bed 21.

In the radiography system 1, a radiation detector 20 is not fixed and supported. The radiation detector 20 is loaded on a carrier by a radiographer or is carried alone by the radiographer and is then transported to a hospital room. When a radiographic image is captured, the radiation detector 20 is provided between the bed 21 and the subject M who lies on the bed. The radiation detector 20 detects radiation which has been emitted from the radiation emitting unit 15 that is located at a position corresponding to the part, of which the image is to be captured, in the subject M with the movement of the movable carriage 11 and then passed through the subject M.

In FIG. 1, the radiation detector 20 is placed on the bed 21 and the subject M lies on the radiation detector 20. However, the radiation detector 20 may be provided in the bed 21.

The radiation detector 20 repeatedly perform a process of recording and reading a radiographic image and may be a so-called direct radiation detector which directly receives radiation and generates charge or a so-called indirect radiation detector which converts radiation into visible light and converts the visible light into a charge signal. In addition, as a method for reading a radiographic image signal, it is preferable to use a so-called thin film transistor (TFT) reading method which turns on and off a TFT switch to read a radiographic image signal or a so-called optical reading method which emits reading light to read a radiographic image signal. However, the invention is not limited thereto. Other methods may be used.

In this embodiment, a scattered radiation removal grid for removing a radiation component which is scattered by the subject M among radiation components that pass through the subject M is not provided between the subject M and the radiation detector 20.

The radiation detector 20 is connected to the control device 12 by a cable 26 or wirelessly. The control device 12 includes a detector controller 33 that controls the reading of a charge signal from the radiation detector 20. In addition, the control device 12 is provided with, for example, a circuit board including a charge amplifier which converts the charge signal read from the radiation detector 20 into a voltage signal, a correlated double sampling circuit which samples the voltage signal output from the charge amplifier, and an A/D converter which converts the voltage signal into a digital signal.

When the radiography system 1 is used, an imaging request is input to the radiography system 1. The imaging request includes information about the name of the patient, of which the radiographic image is to be captured, and an imaging procedure (for example, posteroanterior chest radiography and lateral chest radiography). The imaging request is transmitted from the center console PC 5 which is installed in the hospital or a radiology information system (hereinafter, referred to as a "RIS") which manages information, such as appointment for medical services and diagnostic records in the department of radiology in the hospital, through a network. The operator moves the radiographic image processing system 1 to the hospital room in which the patient is located, on the basis of the imaging request, installs the radiation detector 20 on the basis of the imaging procedure, and captures a radiographic image.

Figure 2:
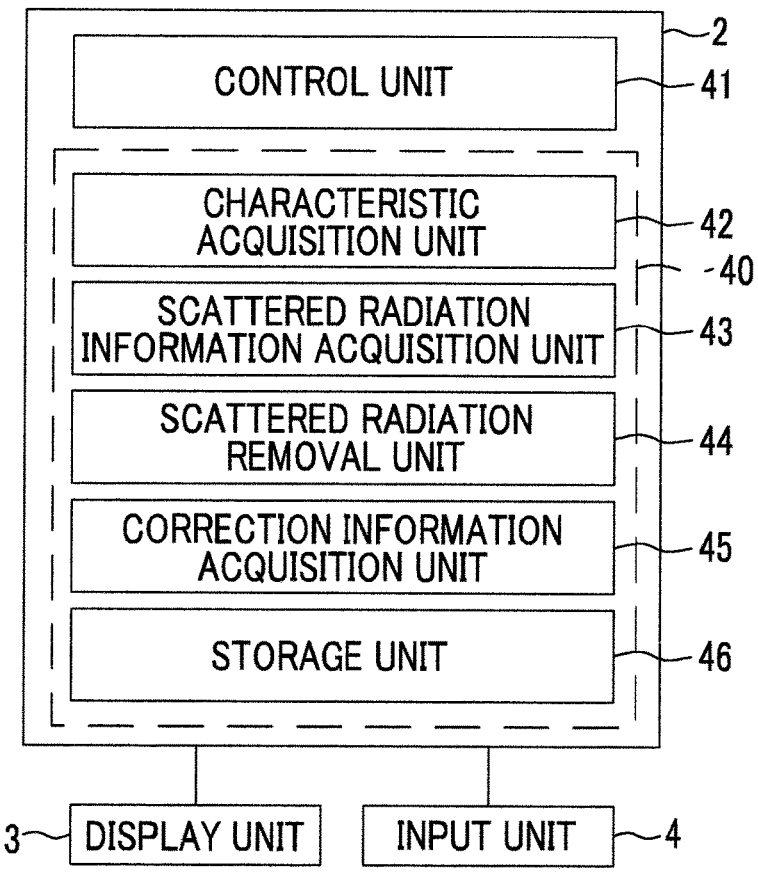
FIG. 2 is a block diagram schematically illustrating the internal structure of a computer of the radiography system according to the first embodiment.

The computer 2 includes, for example, a central processing unit (CPU), a semiconductor memory, a communication interface, and a storage device, such as a hard disk or an SSD. A control unit 41, a characteristic acquisition unit 42, a scattered radiation information acquisition unit 43, a scattered radiation removal unit 44, a correction information acquisition unit 45, and a storage unit 46 illustrated in FIG. 2 are implemented by these hardware components. The characteristic acquisition unit 42, the scattered radiation information acquisition unit 43, the scattered radiation removal unit 44, the correction information acquisition unit 45, and the storage unit 46 form a radiographic image processing device 40 according to the invention.

The control unit 41 outputs a predetermined control signal to various controllers 31 to 33 and controls the overall operation of the system.

The characteristic acquisition unit 42 acquires virtual grid characteristics which are the characteristics of a virtual grid assumed to be used in order to remove scattered radiation when a radiographic image is captured.

The scattered radiation information acquisition unit 43 acquires scattered component information indicating a scattered component of radiation included in a radiographic image.

The scattered radiation removal unit 44 performs a scattered radiation removal process for the radiographic image acquired by the radiation detector 20, on the basis of the virtual grid characteristics acquired by the characteristic acquisition unit 42 and the scattered component information acquired by the scattered radiation information acquisition unit 43.

The correction information acquisition unit 45 acquires correction information for correcting the degree of correction of the scattered component and changes imaging conditions on the basis of the acquired correction information through the process which will be described below.

The storage unit 46 stores various kinds of information, such as a table in which defaults imaging conditions are associated with various imaging procedures.

The display unit 3 is, for example, a CRT display or a liquid crystal display and assists the display of a captured radiographic image and various inputs required for a scattered radiation removal process which will be described below. The input unit 4 is, for example, a keyboard, a mouse, or a touch panel.

In this embodiment, the radiographic image processing device 40 performs the scattered radiation removal process for a photographic image which is captured, without using a grid, such that the same scattered radiation removal effect as that of when a photographic image is actually captured using a grid is obtained. The radiographic image processing device 40 performs the scattered radiation removal process, on the basis of the virtual grid characteristics, unlike the methods disclosed in U.S. Pat. No. 8,064,676A, JP1994-014911A (JP-H06-014911A), and C. Fivez et al., "Multi-resolution contrast amplification in digital radiography with compensation for scattered radiation", 1996, pp. 339-342. Therefore, the characteristic acquisition unit 42 acquires the virtual grid characteristics. In this embodiment, the virtual grid characteristics include scattered radiation transmittance Ts for the virtual grid and the transmittance (primary radiation transmittance) Tp of primary radiation which passes through the subject M and is directly emitted to the radiation detector 20. In addition, it is assumed that the values of the scattered radiation transmittance Ts and the primary radiation transmittance Tp are in the range of 0 to 1.

The characteristic acquisition unit 42 may directly receive the values of the scattered radiation transmittance Ts and the primary radiation transmittance Tp from the input unit 4 to acquire the virtual grid characteristics. In this embodiment, the characteristic acquisition unit 42 acquires the virtual grid characteristics, that is, the scattered radiation transmittance Ts and the primary radiation transmittance Tp, on the basis of the imaging conditions.

The imaging conditions include at least one of a source-image receptor distance (SID) during imaging, a tube voltage, an mAs value (tube current-time product), the target of the radiation source, a material forming a filter, or the type of radiation detector used for imaging. Here, when a radiographic image is captured, the imaging conditions are determined according to an imaging procedure and the type of grid used is determined according to the imaging conditions. In addition, the type of grid varies depending on, for example, a grid ratio, grid density, information indicating whether the grid is a convergence type or a parallel type, a focusing distance in a case in which the grid is a convergence type, and an interspace material (for example, aluminum, fiber, or Bakelite). The scattered radiation transmittance Ts and the primary radiation transmittance Tp vary depending on the type of grid. Therefore, in this embodiment, a table in which various imaging procedures are associated with the imaging conditions and a table in which various imaging conditions are associated with the virtual grid characteristics are stored in the storage unit 46. FIG. 3 is a diagram illustrating the table in which various imaging procedures are associated with the imaging conditions. In a table LUT1 illustrated in FIG. 3, various imaging procedures, such as posteroanterior chest radiography and lateral chest radiography, are associated with the imaging conditions (a tube voltage and an mAs value).

The characteristic acquisition unit 42 acquires the imaging conditions from the imaging procedure, with reference to the table LUT1 in which various imaging procedures and the imaging conditions are associated with each other and which is stored in the storage unit 46, and acquires the virtual grid characteristics from the imaging conditions with reference to the table in which various imaging conditions and the virtual grid characteristics are associated with each other.

In this embodiment, the scattered radiation removal process is performed by performing frequency decomposition for the radiographic image, which will be described below. In this embodiment, the virtual grid characteristics are acquired for each of a plurality of frequency bands of the radiographic image obtained by frequency decomposition. Therefore, the virtual grid characteristics are associated with each of the plurality of frequency bands in the table in which various imaging conditions and the virtual grid characteristics are associated with each other.

In this embodiment, the radiographic image processing device 40 performs the scattered radiation removal process on the basis of the scattered component information, in addition to the virtual grid characteristics. Therefore, the scattered radiation information acquisition unit 43 acquires the scattered component information. In this embodiment, it is assumed that the scattered component information is a scattered radiation content distribution in the radiographic image. In the scattered radiation content distribution, for example, if the subject M is the chest, the amount of scattered radiation increases toward the center of the radiographic image at which a mediastinal part is present and the amount of scattered radiation decreases toward the periphery of the radiographic image in which the lung field is present.

The scattered radiation information acquisition unit 43 analyzes the captured radiographic image to acquire the scattered component information, that is, the scattered radiation content distribution. The radiographic image is analyzed on the basis of irradiation field information, the subject information, and the imaging conditions when the radiographic image is captured.

The irradiation field information is information indicating an irradiation field distribution related to the position and size of the irradiation field which is included in the radiographic image when imaging is performed using an irradiation field diaphragm. The subject information is information related to, for example, the position of the subject on the radiographic image, the distribution of the composition of the subject, the size of the subject, the thickness of the subject, in addition to the type of subject, such as the chest, the abdomen, or the head. The imaging conditions include information related to, for example, an air gap (the distance from the subject to the radiation detector) and the characteristics of the radiation detector, in addition to a tube voltage, an mAs value, and a source-image receptor distance (the sum of the distance from the radiation source to the subject and the distance from the subject to the radiation detector). The irradiation field information, the subject information, and the imaging conditions are factors for determining the distribution of the scattered radiation included in the radiographic image. For example, the amount of scattered radiation depends on the magnitude of the irradiation field. As the thickness of the subject increases, the amount of scattered radiation increases. If there is air between the subject and the radiation detector, the amount of scattered radiation decreases.

Therefore, the use of these information items makes it possible to accurately acquire the scattered radiation content distribution.

The scattered radiation information acquisition unit 43 calculates a primary radiation image and a scattered radiation image from the distribution T(x, y) of the thickness of the subject in the captured radiographic image, on the basis of the following Expressions (1) and (2), and calculates a scattered radiation content distribution S(x, y) from the calculated primary radiation image and scattered radiation image, on the basis of Expression (3). The scattered radiation content distribution S(x, y) has a value of 0 to 1.

$$Icp(x, y)=Io(x, y) \times \exp(-\mu \times T(x, y)) \quad (1)$$

$$Ics(x, y)=Io(x, y) * S\sigma(T(x, y)) \quad (2)$$

$$S(x, y)=Ics(x, y)/(Ics(x, y)+Icp(x, y)) \quad (3)$$

Here, (x, y) is the coordinates of a pixel position in a radiographic image, Icp(x, y) is a primary radiation image at the pixel position (x, y), Ics(x, y) is a scattered radiation image at the pixel position (x, y), Io(x, y) is an incident dose on the surface of the subject at the pixel position (x, y), μ is a linear attenuation coefficient of the subject, and Sσ(T(x, y)) is a convolution kernel indicating scattering characteristics corresponding to the thickness of the subject at the pixel position (x, y). Expression (1) is based on a known exponential attenuation rule and Expression (2) is based on the method described in "J. M. Boon et al., An analytical model of the scattered radiation distribution in diagnostic radiolog, Med. Phys. 15(5), September/October 1988" (Reference Document 1). Even if the incident dose Io(x, y) on the surface of the subject is defined as any value, the incident dose Io(x, y) is cancelled by division when S(x, y) is calculated. Therefore, the incident dose Io(x, y) may be set to an arbitrary value, for example, 1.

The distribution T(x, y) of the thickness of the subject may be calculated by converting the pixel value of the radiographic image into a thickness, using the linear attenuation coefficient, on the assumption that a brightness distribution in the radiographic image is substantially identical to the distribution of the thickness of the subject. Alternatively, the thickness of the subject may be measured using, for example, a sensor or may be approximated by a model, such as a cube or an elliptic cylinder.

In Expression (2), * is an operator indicating a convolution operation. The properties of a kernel change depending on, for example, the distribution of the irradiation field, the distribution of the composition of the subject, and the imaging conditions (that is, the tube voltage during imaging, the mAs value, the source-image receptor distance, the air gap, and the characteristics of the radiation detector), in addition to the thickness of the subject. According to the method described in Reference Document 1, scattered radiation can be approximated by the convolution of a point spread function (Sσ(T(x, y)) in Expression (2)) with respect to the primary radiation. In addition, Sσ(T(x, y)) can be experimentally calculated on the basis of, for example, the irradiation field information, the subject information, the imaging conditions.

In this embodiment, Sσ(T(x, y)) may be calculated on the basis of the irradiation field information, the subject information, and the imaging conditions during imaging. A table in which various kinds of irradiation field information, various kinds of subject information, and various imaging conditions are associated with Sσ(T(x, y)) may be stored in the storage unit 46 and Sσ(T(x, y)) may be calculated on the basis of the irradiation field information, the subject information, and the imaging conditions during imaging, with reference to the table. In addition, Sσ(T(x, y)) may be approximated by T(x, y).

The scattered radiation removal unit 44 reduces a frequency component in a frequency band which is regarded as scattered radiation in the radiographic image, on the basis of the virtual grid characteristics and the scattered component information, thereby performing the scattered radiation removal process. The scattered radiation removal unit 44 performs frequency decomposition for the radiographic image to acquire frequency components for a plurality of frequency bands, reduces the gain of at least one frequency component, and synthesizes the processed frequency component and the other frequency components to acquire a radiographic image subjected to the scattered radiation removal process. As a frequency decomposition method, in addition to a method for performing multi-resolution conversion for the radiographic image, other known methods, such as wavelet transform and Fourier transform, can be used.

The scattered radiation removal unit 44 calculates a conversion coefficient R(x, y) for converting a frequency component from the scattered radiation transmittance Ts and the primary radiation transmittance Tp, which are the virtual grid characteristic, and the scattered radiation content distribution S(x, y), using the following Expression (4).

$$R(x, y)=S(x, y) \times Ts+(1-S(x, y)) \times Tp \quad (4)$$

Since each of the scattered radiation transmittance Ts, the primary radiation transmittance Tp, and the scattered radiation content distribution S(x, y) has a value of 0 to 1, the conversion coefficient R(x, y) also has a value of 0 to 1. The scattered radiation removal unit 44 calculates the conversion coefficient R(x, y) for each of a plurality of frequency bands.

In the following description, it is assumed that the pixel value of a radiographic image is represented by I(x, y), a frequency component image obtained by frequency decomposition is represented by I(x, y, r), frequency synthesis is represented by I(x, y)=ΣrI(x, y, r), a conversion coefficient for each frequency band is represented by R(x, y, r), and the scattered radiation transmittance and the primary radiation transmittance of each frequency band are represented by Ts(r) and Tp(r), respectively. In addition, "r" indicates the layer of a frequency band. As r becomes greater, the frequency becomes lower. Therefore, I(x, y, r) indicates a frequency component image of a certain frequency band.

The scattered radiation content distribution S(x, y) for the radiographic image may be used without any change, or may be acquired for each frequency band, similarly to the scattered radiation transmittance Ts and the primary radiation transmittance Tp.

In this embodiment, the conversion coefficient R(x, y, r) is calculated for each frequency component and the frequency component image I(x, y, r) is multiplied by the conversion coefficient R(x, y, r) of the corresponding frequency band to convert the pixel value of the frequency component image I(x, y, r). Then, frequency synthesis is performed for the frequency component image I(x, y, r) multiplied by the conversion coefficient R(x, y, r) (that is, I(x, y, r)×R(x, y, r)) to acquire a processed radiographic image I'(x, y). Therefore, the process which is performed by the scattered radiation removal unit 44 is represented by the following Expression (5). Since the conversion coefficient R(x, y, r) has a value of 0 to 1, the pixel value of the frequency component at the pixel position (x, y), that is, the gain is reduced by multiplying the frequency component (x, y, r) by the conversion coefficient R(x, y, r) of the corresponding frequency band.

$$I'(x, y) = \Sigma r\{I(x, y, r) \times R(x, y, r)\} \quad (5)$$
$$= \Sigma r\{I(x, y, r) \times (S(x, y) \times Ts(r) + (1 - S(x, y)) \times Tp(r))\}$$

In this embodiment, it is assumed that the radiographic image is decomposed into six frequency bands and the scattered radiation transmittance Ts and the primary radiation transmittance Tp are acquired for the six frequency bands. In this case, the scattered radiation transmittance Ts and the primary radiation transmittance Tp have, for example, values shown in the following Expression (6). In Expression (6), it is assumed that a value closer to the right side indicates a lower frequency band.

$$Ts=\{0.7,0.7,0.7,0.7,0.3,0.2\}$$
$$Tp=\{0.7,0.7,0.7,0.7,0.7,0.7\} \quad (6)$$

As shown in Expression (6), the scattered radiation transmittance Ts and the primary radiation transmittance Tp have the same value in a high frequency band (r=1 to 4) and the scattered radiation transmittance Ts is lower than the primary radiation transmittance Tp in a low frequency band (r=5 to 6). The reason is that the grid has a higher removal rate in a lower frequency band in which the frequency component of the scattered radiation is dominant and the dependence of the removal rate of the grid for the primary radiation on the frequency is low.

Figure 4:
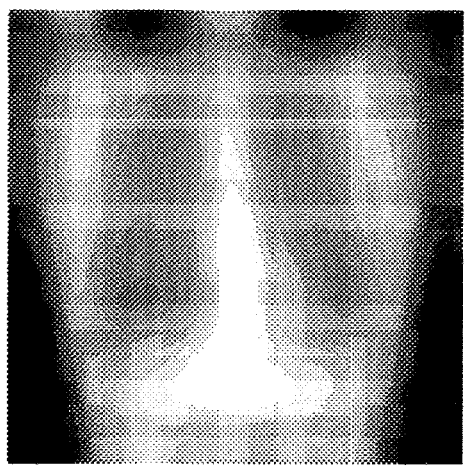
FIG. 4 is a diagram illustrating a scattered radiation content distribution in a radiographic image of the chest.
Figure 5:
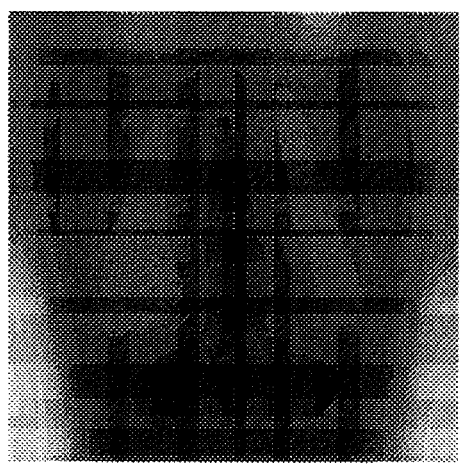
FIG. 5 is a diagram illustrating a conversion coefficient which is calculated in a case in which the scattered radiation content distribution illustrated in FIG. 4 is shown.

FIG. 4 is a diagram illustrating a scattered radiation content distribution S(x, y) in a radiographic image of the chest. In FIG. 4, as the scattered radiation content distribution S(x, y) becomes higher, brightness at each pixel position becomes higher. As can be seen from FIG. 4, in the image of the chest, the content of scattered radiation in the mediastinal part and around the lung field is high. FIG. 5 illustrates the conversion coefficient which is calculated on the basis of Expressions (4) and (6) in a case in which the scattered radiation content distribution S(x, y) is represented. In FIG. 5, as brightness becomes lower, the value of the conversion coefficient becomes smaller and the pixel value is more significantly reduced. As can be seen from the comparison between FIG. 4 and FIG. 5, the value of the conversion coefficient is small in the mediastinal portion and around the lung field where the content of scattered radiation is high. Therefore, in the processed radiographic image acquired by performing the process shown in Expression (5) using the conversion coefficient calculated in this way, a scattered component is removed according to the type of grid to be used.

The scattered radiation removal unit 44 may remove the scattered radiation of the radiographic image as follows. First, similarly to the above, if frequency synthesis is represented by I(x, y)=ΣrI(x, y, r), the scattered radiation removal unit 44 decomposes the frequency component image I(x, y, r) into a scattered component Ics(x, y, r) and a primary radiation component Icp(x, y, r) on the basis of the scattered radiation content distribution S(x, y), using the following Expression (7).

$$Ics(x, y, r)=S(x, y)\times I(x, y, r)$$
$$Icp(x, y, r)=(1-S(x, y))\times I(x, y, r) \quad (7)$$

The scattered radiation removal unit 44 applies the scattered radiation transmittance Ts(r) and the primary radiation transmittance Tp(r), which are the virtual grid characteristics, to the scattered component Ics(x, y, r) and the primary radiation component Icp(x, y, r), respectively, to perform image conversion, thereby calculating a converted scattered component Ics'(x, y, r) and a converted primary radiation component Icp'(x, y, r), using the following Expression (8).

$$Ics'(x, y, r)=Ics(x, y, r)\times Ts(r)=S(x, y)\times I(x, y, r)\times Ts(r)$$

$$Icp'(x, y, r)=Icp(x, y, r)\times Tp(r)=(1-S(x, y))\times I(x, y, r)\times Tp(r) \quad (8)$$

Then, the scattered radiation removal unit 44 performs frequency synthesis for the scattered component Ics'(x, y, r) and the primary radiation component Icp'(x, y, r) to calculate a processed radiographic image I'(x, y), using the following Expression (9).

$$I'(x, y) = \Sigma r\{Ics'(x, y, r) + Icp'(x, y, r)\} \quad (9)$$
$$= \Sigma r\{S(x, y) \times I(x, y, r) \times Ts(r) + (1 - S(x, y)) \times I(x, y, r) \times Tp(r)\}$$
$$= \Sigma r\{I(x, y, r) \times (S(x, y) \times Ts(r) + (1 - S(x, y)) \times Tp(r))\}$$

In this embodiment, the scattered radiation removal process is performed using the imaging conditions corresponding to the imaging procedure. However, in some cases, during an actual imaging process, the imaging conditions are changed depending on the body type of the subject M and then imaging is performed. For example, in the case of a fat patient, the tube voltage and the mAs value increase. In the case of a thin patient, the tube voltage and the mAs value decrease. In this case, the imaging conditions corresponding to the imaging procedure are different from the imaging conditions which are currently used. Therefore, when the scattered radiation removal process is performed using the imaging conditions corresponding to the imaging procedure, it is difficult to remove a scattered component with high accuracy. As a result, it is difficult to obtain a radiographic image with desired quality.

The correction information acquisition unit 45 acquires correction information for correcting the degree of removal of the scattered component. FIG. 6 is a diagram illustrating a confirmation screen for describing the acquisition of the correction information. As illustrated in FIG. 6, a confirmation screen 50 which is displayed on the display unit 3 includes an image display region 51 in which a processed radiographic image is displayed, a body type selection region 52 for selecting the body type of the subject M, a confirmation completion button 53, a correction button 54, and a re-imaging button 55. Five icons indicating a fat body type, a slightly fat body type, a normal body type, a slightly thin body type, and a thin body type are displayed in the body type selection region 52 in order to input the body type of the subject M.

In a case in which the degree of removal does not need to be corrected, the operator selects the confirmation completion button 53. Then, the radiographic image processing device 40 ends the scattered radiation removal process. On the other hand, when the degree of removal needs to be corrected, the operator uses the input unit 4 to move a pointer 57 to the body type selection region 52, selects an icon indicating the desired body type, and selects the correction button 54. Then, the correction information acquisition unit 45 acquires information about the selected body type (fat, slightly fat, normal, slightly thin, and thin) as the correction information. Then, the correction information acquisition unit 45 changes the imaging conditions corresponding to the imaging procedure, on the basis of the acquired correction information, and outputs the changed imaging conditions to the characteristic acquisition unit 42, the scattered radiation information acquisition unit 43, and the scattered radiation removal unit 44.

Specifically, in a case in which the correction information indicates "fat", the correction information acquisition unit 45 changes the imaging conditions such that the tube voltage and the mAs value increase. In a case in which the correction information indicates "thin", the correction information acquisition unit 45 changes the imaging conditions such that the tube voltage and the mAs value decrease. In this embodiment, a table LUT2 in which the correction information (that is, fat, slightly fat, normal, slightly thin, and thin) and the imaging conditions are associated with each other is stored in the storage unit 46. FIG. 7 is a diagram illustrating a table in which various kinds of correction information and the imaging conditions are associated with each other. As illustrated in FIG. 7, in the table LUTZ, the correction information and the imaging conditions are associated with each other. In addition, in the table LUT2, the correction information and the imaging conditions are associated with each imaging procedure. The correction information acquisition unit 45 acquires the changed imaging conditions with reference to the table LUT2.

The characteristic acquisition unit 42 acquires the virtual grid characteristics on the basis of the changed imaging conditions. The scattered radiation removal unit 44 calculates the kernel Sσ(T(x, y)) on the basis of the changed imaging conditions, calculates a new scattered radiation content distribution S(x, y), using the above-mentioned Expressions (1) to (3), and acquires a new processed radiographic image I'(x, y), using Expressions (4) and (5).

Figure 8:
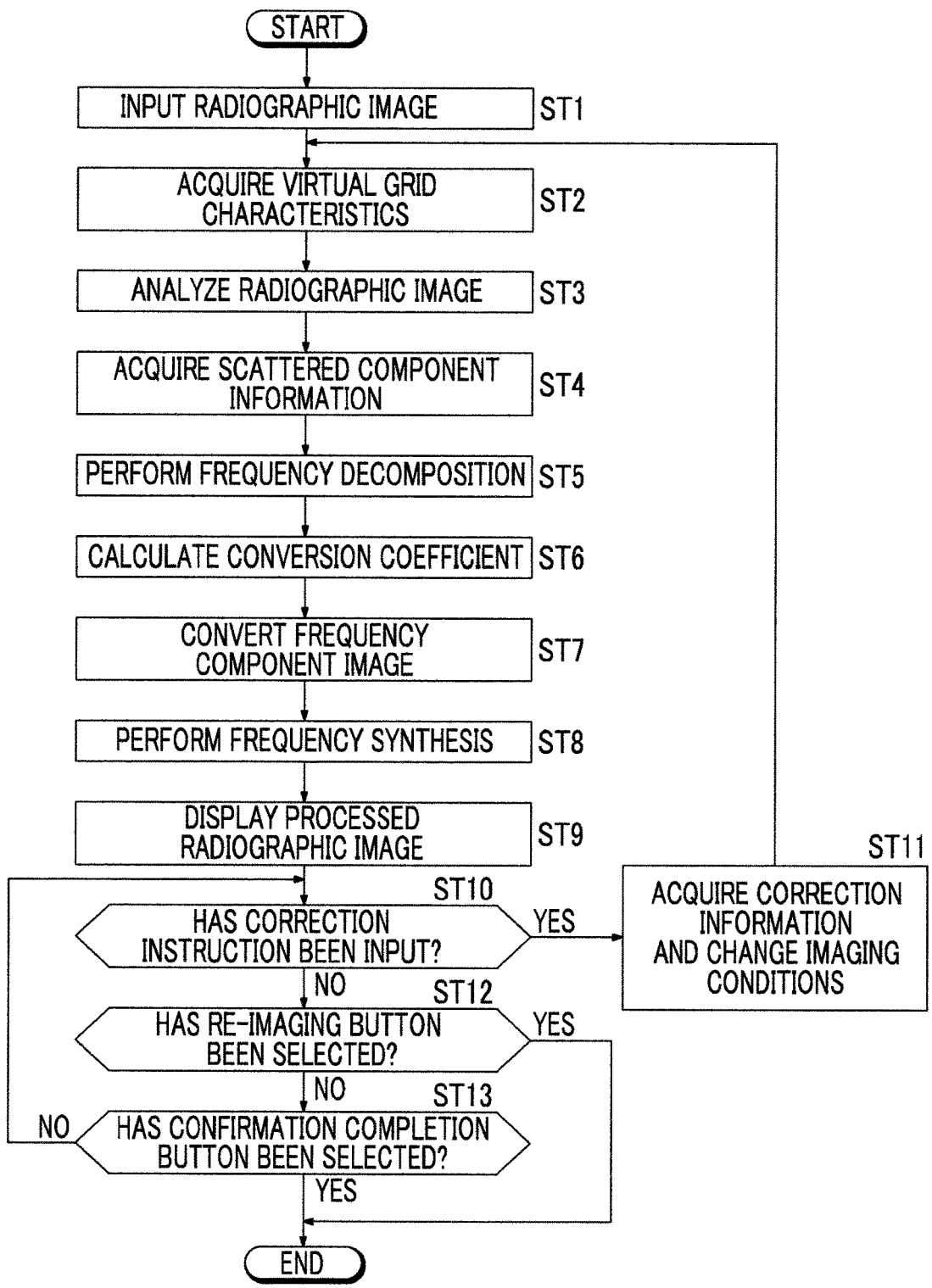
FIG. 8 is a flowchart illustrating a process which is performed in the first embodiment.

Next, a process which is performed in the first embodiment will be described. FIG. 8 is a flowchart illustrating the process performed in the first embodiment. A radiographic image of the subject M is captured, using the imaging conditions corresponding to an imaging procedure, on the basis of an imaging request. When the radiographic image is input to the computer 2 (Step ST1), the characteristic acquisition unit 42 acquires the virtual grid characteristics, that is, the scattered radiation transmittance Ts and the primary radiation transmittance Tp, on the basis of the imaging conditions corresponding to the imaging procedure (Step ST2).

The scattered radiation information acquisition unit 43 analyzes the radiographic image (Step ST3) and acquires scattered component information, that is, a scattered radiation content distribution S(x, y) (Step ST4). The scattered radiation removal unit 44 performs frequency decomposition for the radiographic image (Step ST5). The process in Step ST2, the process in Steps ST3 and ST4, and the process in Step ST5 may be performed in parallel. Alternatively, the process in Steps ST3 and ST4 may be performed first and the process in Step ST5 may be performed later.

Then, the scattered radiation removal unit 44 calculates a conversion coefficient R(x, y, r) for each frequency band, using the above-mentioned Expression (4) (Step ST6), and converts a frequency component image I(x, y, r), using the conversion coefficient R(x, y, r) (Step ST7). Then, frequency synthesis is performed for a converted frequency component image I'(x, y, r) to acquire a processed radiographic image (Step ST8) and the processed radiographic image is displayed on the display unit 3 (Step ST9).

Then, the control unit 41 determines whether a body type correction instruction has been received (Step ST10). When the determination result in Step ST10 is "Yes", the correction information acquisition unit 45 acquires correction information and changes the imaging conditions on the basis of the correction information (Step ST11). Then, the process returns to Step ST2 and the characteristic acquisition unit 42, the scattered radiation information acquisition unit, 43 and the scattered radiation removal unit 44 perform the process from Step ST2 to Step ST9, on the basis of the changed imaging conditions. When the determination result in Step ST10 is "No", the control unit 41 determines whether the re-imaging button 55 has been selected (Step ST12). When the determination result in Step ST12 is "Yes", the control unit 41 ends the process for re-imaging. When the determination result in Step ST12 is "No", the control unit 41 determines whether the confirmation completion button 53 has been selected (Step ST13). When the determination result in Step ST13 is "No", the process returns to Step ST10. On the other hand, when the determination result in Step ST13 is "Yes", the process ends. The processed radiographic image is transmitted to the center console PC 5 and is then stored therein.

As such, in the first embodiment, the scattered component that is included in the radiation, which has passed through the subject during imaging, in the radiographic image is removed on the basis of the imaging conditions corresponding to the imaging procedure. When the correction information for corresponding to the degree of removal of the scattered component is acquired, the imaging conditions corresponding to the imaging procedure are changed on the basis of the correction information and the scattered component is removed from the radiographic image. Therefore, it is possible to appropriately remove a scattered component according to the correction information. As a result, it is possible to acquire a high-quality radiographic image.

Figure 9:
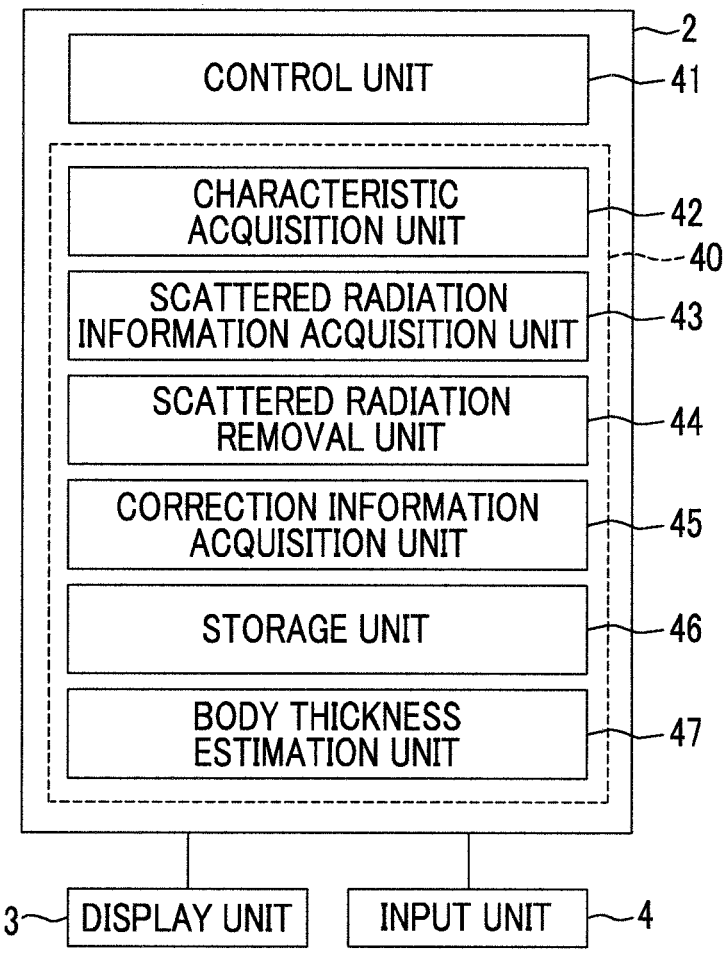
FIG. 9 is a block diagram schematically illustrating the internal structure of a computer of a radiography system according to a second embodiment.

Next, a second embodiment of the invention will be described. FIG. 9 is a block diagram schematically illustrating the internal structure of a computer in a radiography system according to the second embodiment of the invention. As illustrated in FIG. 9, the second embodiment differs from the first embodiment in that it includes a body thickness estimation unit 47 which analyzes a radiographic image to estimate a body thickness distribution of a subject M.

Figure 10:
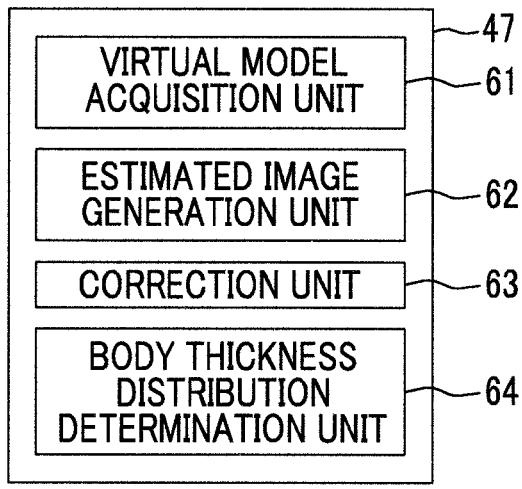
FIG. 10 is a block diagram schematically illustrating the structure of a body thickness estimation unit.

FIG. 10 is a block diagram schematically illustrating the structure of the body thickness estimation unit. As illustrated in FIG. 10, the body thickness estimation unit 47 includes a virtual model acquisition unit 61, an estimated image generation unit 62, a correction unit 63, and a body thickness distribution determination unit 64.

The virtual model acquisition unit 61 acquires a virtual model K of the subject M having an initial body thickness distribution $T_0$ (predetermined body thickness distribution).

The estimated image generation unit 62 generates a composite image of an estimated primary radiation image Ip, which is obtained by estimating a primary radiation image obtained by radiography of the virtual model, and an estimated scattered radiation image Is, which is obtained by estimating a scattered radiation image obtained by radiography for the virtual model, as an estimated image Im which is obtained by estimating a radiographic image obtained by radiography for the subject M, on the basis of the virtual model K.

The correction unit 63 corrects the initial body thickness distribution $T_0$ of the virtual model K such that the difference between the estimated image Im and the radiographic image is reduced, on the basis of the estimated image Im and the radiographic image.

The body thickness distribution determination unit 64 determines a corrected body thickness distribution Tn−1 (n is a natural number) as the body thickness distribution Tk of the radiographic image.

In the second embodiment, the storage unit 46 stores the virtual model K of the subject M having the initial body thickness distribution $T_0(x, y)$. The body thickness means the total thickness of a subject region except for an air region on the path of the emitted radiation.

Figure 11:
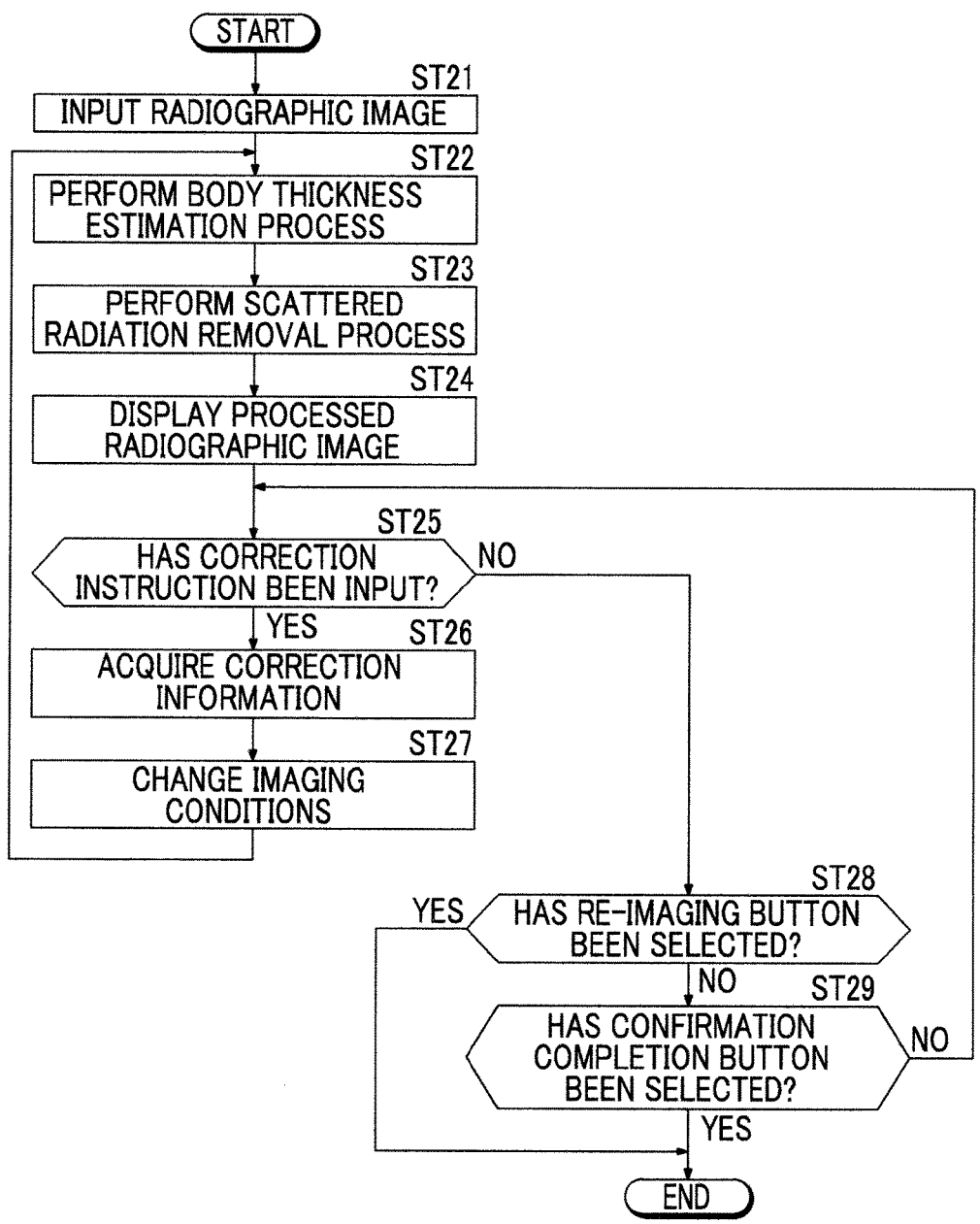
FIG. 11 is a flowchart illustrating a process which is performed in the second embodiment.

Next, a process which is performed in the second embodiment will be described. FIG. 11 is a flowchart illustrating the process performed in the second embodiment. A radiographic image of the subject M is captured using the imaging conditions corresponding to an imaging procedure. When the radiographic image is input to the computer 2 (Step ST21), the body thickness estimation unit 47 performs a body thickness estimation process (Step ST22).

Figure 12:
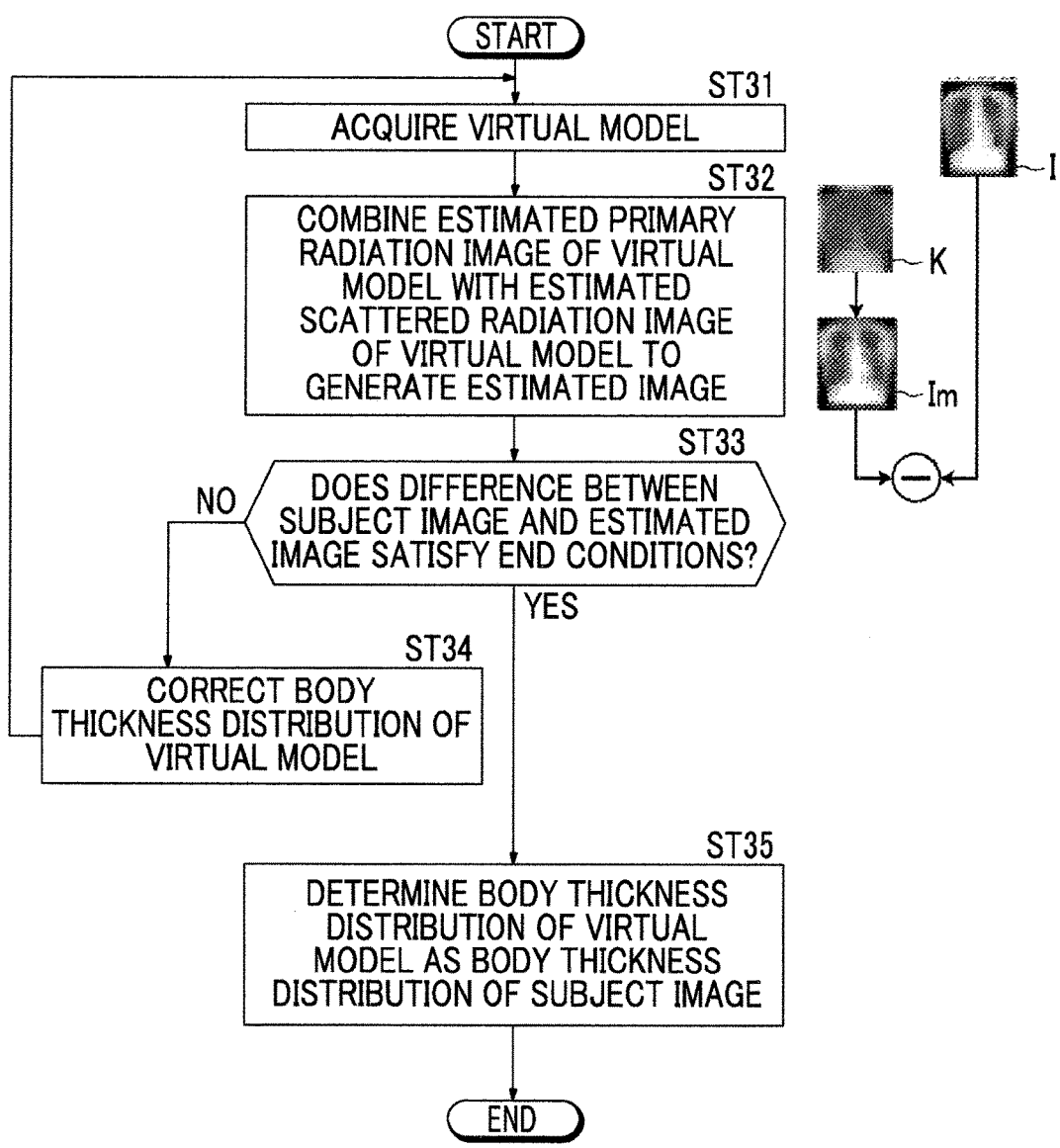
FIG. 12 is a flowchart illustrating a body thickness estimation process.

FIG. 12 is a flowchart illustrating the body thickness estimation process. The virtual model acquisition unit 61 of the body thickness estimation unit 47 acquires the virtual model K of the subject M having the initial body thickness distribution $T_0(x, y)$ from the storage unit 46 (Step ST31). The virtual model K is data which virtually indicates the subject M and in which a body thickness that follows the initial body thickness distribution $T_0(x, y)$ is associated with each position on an x-y plane. In addition, structures (here, anatomic structures such as a lung field, a bone, and an organ) included in the virtual model K, the arrangement of the structures, and characteristic information indicating, for example, the characteristics of the structures with respect to radiation are set on the basis of the arrangement and composition of anatomic structures, such as the lung field of the chest and abdomen of a comparative subject and the bones.

Figure 13:
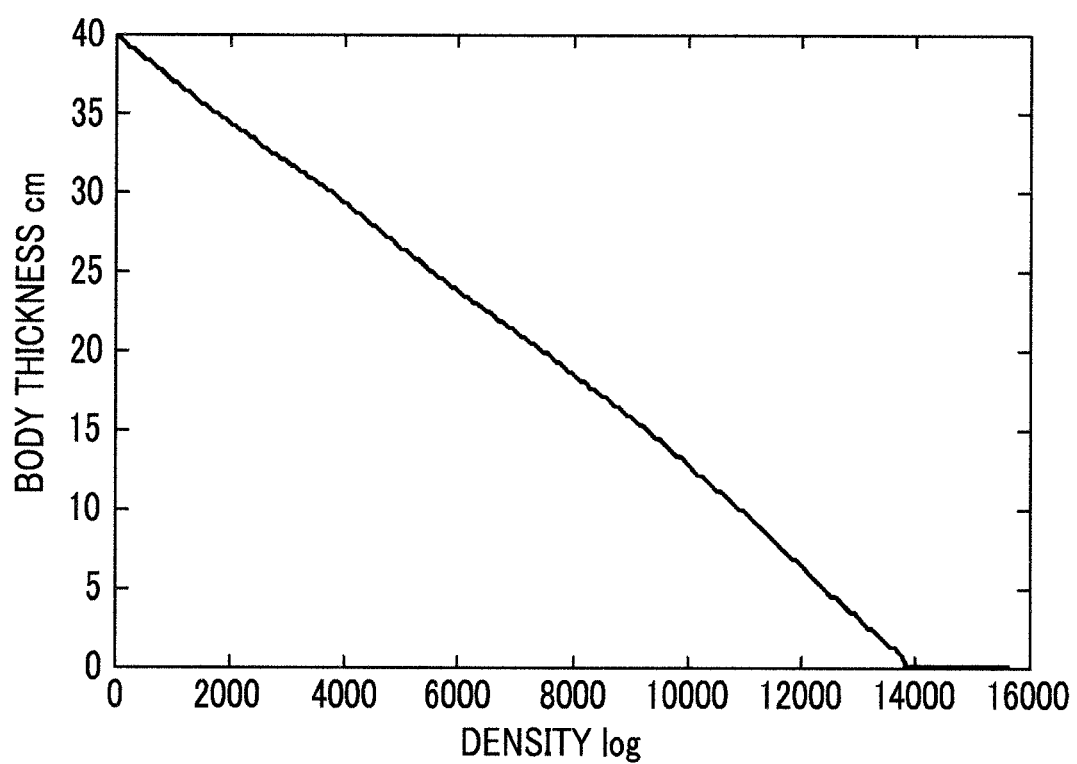
FIG. 13 is a diagram illustrating an example of a body thickness distribution correspondence table.

The virtual model K may have any initial body thickness distribution $T_0(x, y)$. However, in this embodiment, the initial body thickness distribution $T_0$ is generated and acquired by the virtual model acquisition unit 61. The virtual model acquisition unit 61 acquires imaging conditions, such as the radiation dose of the subject M, a tube voltage, and an SID, and acquires a table in which the pixel value corresponding to the imaging conditions of the subject M is associated with the body thickness from the storage unit 46. In this case, the imaging conditions correspond to the imaging procedure. FIG. 13 illustrates an example of the table in which the pixel value is associated with the body thickness. Then, the virtual model acquisition unit 61 specifies the body thickness corresponding to the value of each pixel in the radiographic image of the subject M on the basis of the table illustrated in FIG. 13 to acquire the body thickness distribution of the radiographic image. Then, the virtual model acquisition unit 61 acquires the body thickness distribution of the radiographic image as the initial body thickness distribution $T_0$ (predetermined body thickness distribution) of the virtual model K. The initial body thickness distribution $T_0$ may be generated during the process of acquiring the virtual model K as in this embodiment, or may be set before the process of acquiring the virtual model K in advance. The above-mentioned process is represented by the following Expression (11). In addition, I(x, y) indicates the value of each pixel in a radiographic image and $T_0(x, y)$ indicates an initial body thickness distribution at each pixel position.

$$T_0(x,y)=LUT(I(x,y)) \tag{11}$$

Figure 14:
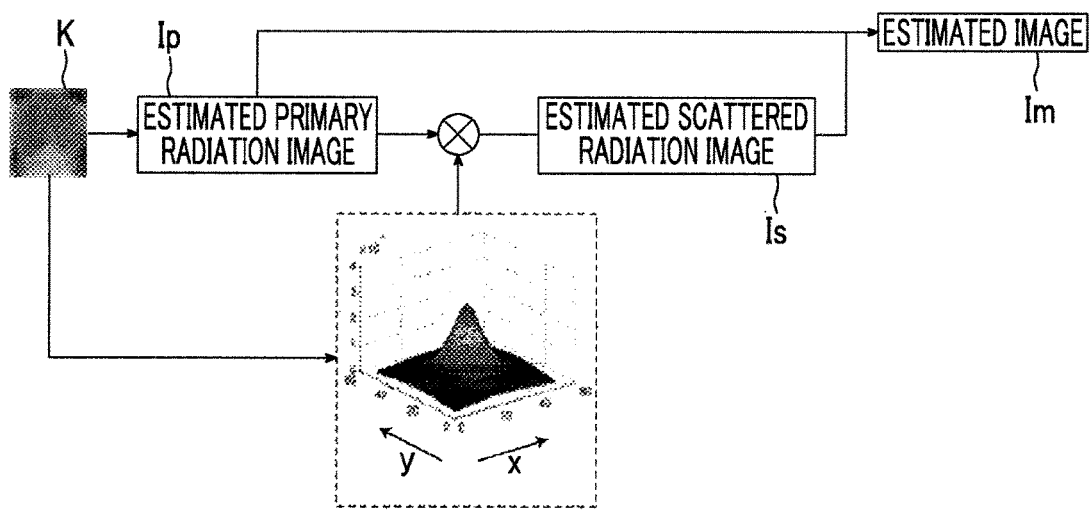
FIG. 14 is a diagram illustrating an example of an estimated image generation method.
Figure 15:
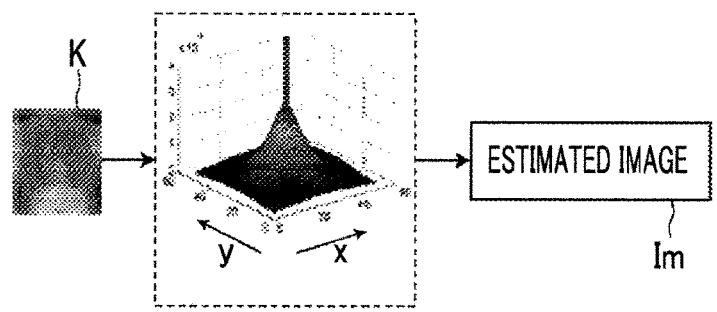
FIG. 15 is a diagram illustrating another example of the estimated image generation method.

Then, the estimated image generation unit 62 combines an estimated primary radiation image Ip, which is obtained in a case in which the image of the virtual model K is captured under the same imaging conditions as the radiographic image, and an estimated scattered radiation image Is, which is obtained in a case in which the image of the virtual model K is captured under the same imaging conditions as the radiographic image, to generate an estimated image Im (Step ST32). FIGS. 14 and 15 are diagrams illustrating a method for generating the estimated image Im.

As illustrated in FIG. 14, the estimated image generation unit 62 generates the estimated primary radiation image Ip, which is obtained in a case in which the image of the virtual model K is captured under the same imaging conditions as the radiographic image, according to the following Expression (12), and generates the estimated scattered radiation image Is using the generated estimated primary radiation image Ip, according to the following Expression (13). Then, the estimated image generation unit 62 combines the estimated primary radiation image Ip and the estimated scattered radiation image Is to generate the estimated image Im, as shown in the following Expression (14) (Step ST32). When the estimated primary radiation image Ip and the estimated scattered radiation image Is are generated first, the initial body thickness distribution $T_0(x, y)$ is used in Estimation Expressions (12) and (13) (n is 1 in Expressions (12) and (13)).

$$I_p(x, y) = I_0(x, y) \times \exp(-T_{n-1}(x, y) \times \mu) \tag{12}$$

$$I_s(x, y) = \sum_{x',y'} I_p(x', y') K_s(x, y, T_{n-1}(x', y'), \theta_{x',y'}) \tag{13}$$

$$I_m(x, y) = I_p(x, y) + I_s(x, y) \tag{14}$$

Here, (x, y) is the coordinates of a pixel position in a radiographic image, Ip(x, y) is an estimated primary radiation image at the pixel position (x, y), Is(x, y) is an estimated scattered radiation image at the pixel position (x, y), Io(x, y) is a dose at the pixel position (x, y), Im(x, y) is an estimated image at the pixel position (x, y), μ is a linear attenuation coefficient of the subject, and Ks(x, y, Tn(x', y'), θx', y') is a convolution kernel indicating a point spread function corresponding to the thickness of the subject at the pixel position (x, y). The dose Io(x, y) is a radiation dose which is detected by the radiation detector 20 on the assumption that no subject is present and varies depending on the distance (SID) between the radiation source 16 and the detection surface of the radiation detector 20, a tube voltage, and an mAs value. In addition, θx', y' indicates a parameter which is specified by the imaging conditions, such as the tube voltage, or the characteristic information of the virtual model K.

In addition, the estimated image Im may be an image which is estimated to be obtained in a case in which the radiographic image of the virtual model K is captured and may be any image which is substantially regarded as a composite image of the estimated primary radiation image Ip and the estimated scattered radiation image Is. For example, as illustrated in FIG. 15, the estimated image Im may be generated by the convolution integral of the kernel combining a primary radiation component and a scattered component, using the following Expression (15), instead of Expressions (12) to (14). Here, Kp+s(x, y, Tn-1(x', y'), θx', y') is a kernel indicating a point spread function that combines the primary radiation component and the scattered component. In addition, any model function may be used as long as it can generate an estimated image obtained by combining the estimated primary radiation image and the estimated scattered radiation image from the image obtained by radiography.

In addition, Ks(x, y, Tn(x', y'), θx', y') and Kp+s(x, y, Tn-1(x', y'), θx', y') can be experimentally calculated according to, for example, imaging conditions.

In this embodiment, the kernels Ks(x, y, Tn(x', y'), θx', y') and Kp+s(x, y, Tn-1(x', y'), θx', y') may be calculated on the basis of the imaging conditions during imaging. A table in which various imaging conditions and the kernels Ks(x, y, Tn(x', y'), θx', y') and Kp+s(x, y, Tn-1(x', y'), θx', y') are associated with each other is stored in the storage unit 46 and the kernels Ks(x, y, Tn(x', y'), θx', y') and Kp+s(x, y, Tn-1(x', y'), θx', y') are calculated on the basis of irradiation field information, subject information, and imaging conditions during imaging, with reference to the table.

$$I_m(x, y) = \sum_{x',y'} K_{p+s}(x, y, T_{n-1}(x', y'), \theta_{x',y'}) \quad (15)$$

The next process will be described with reference to the flowchart illustrated in FIG. 12. Then, the body thickness distribution determination unit 64 determines whether the difference between the radiographic image and the estimated image Im satisfies end conditions (Step ST33). Here, the following error value $V_{error}$ indicating the difference between the radiographic image and the estimated image Im is defined as shown in Expressions (16) and (17). It is determined whether the error value $V_{error}$ is equal to or less than a threshold value as the end conditions. As shown in Expression (17), the sum of the squares of each pixel value of a difference image Id which is obtained by subtracting the estimated image Im from the radiographic image is defined as an error function $f_{error}$. In addition, any determination method may be used as long as it can determine whether or not the difference between the radiographic image and the estimated image Im is small enough to be allowable, as the end conditions.

$$V_{error} = f_{error}(I_m(x, y), I(x, y)) \quad (16)$$

$$f_{error}(I_m(x, y), I(x, y)) = \sum_{x,y} (I_m(x, y) - I(x, y))^2 \quad (17)$$

However, the invention is not limited to the above-mentioned example. For example, the error function $f_{error}$ can be defined by any method which can indicate the difference between the radiographic image and the estimated image Im. For example, as shown in the following Expression (18), the sum of the absolute values of each pixel value of the differential image Id obtained by subtracting the estimated image Im from the radiographic image may be defined as the error function $f_{error}$.

$$f_{error}(I_m(x, y), I(x, y)) = \sum_{x,y} |I_m(x, y) - I(x, y)| \quad (18)$$

In a case in which the error value $V_{error}$ does not satisfy the end conditions (Step ST33; No), the body thickness distribution determination unit 64 performs a correction process of correcting a body thickness distribution Tn-1 (the initial body thickness distribution $T_0$ in a case in which n is 1) (Step ST34).

Any method which can acquire the correction value of each position in the body thickness distribution Tn-1 such that the difference between the radiographic image and the estimated image Im is reduced can be applied in order to perform the process of correcting the body thickness distribution Tn-1. In this embodiment, a process is performed which changes the body thickness distribution Tn-1 of the virtual model K for each partial region including one or more pixels in the virtual model K to calculate the body thickness of the partial region where the difference between the estimated image Im and the radiographic image is small. Then, the body thickness distribution of the virtual model is corrected using the calculated body thickness of each partial region.

Specifically, in this embodiment, it is assumed that the correction value of the body thickness with the body thickness distribution Tn-1 is calculated using the steepest descent method. It is possible to minimize the output value of the error function $f_{error}$ by repeatedly calculating dTn-1(x, y) on the basis of the primary partial differential (gradient) of the error function $f_{error}$ while changing only the body thickness at one specific coordinate point in Tn-1(x, y) among the pixels of the virtual model K, using the following Expressions (19) and (20). Then, the body thickness at one specific coordinate point when the output value of the error function $f_{error}$ is minimized is determined as the correction value of the body thickness at the specific coordinate point. For the other pixels, similarly, the correction value of each body thickness is calculated and the body thickness distribution of each pixel is corrected. In this way, a corrected body thickness distribution Tn is acquired.

$$T_n(x, y) = T_{n-1}(x, y) - \alpha dT_{n-1}(x, y) \quad (19)$$
$$= T_{n-1}(x, y) - \alpha \frac{d}{dT_{n-1}(x, y)} f_{error}$$

$$\frac{d}{dT_{n-1}(x, y)} f_{error} = \quad (20)$$
$$\sum_{x',y'} (I_m(x', y') - I(x', y')) \frac{d}{dT_{n-1}(x, y)} K_{p+s}(x', y', T_{n-1}(x, y), \theta_{x,y})$$

$$\frac{d}{dT_{n-1}(x, y)} K_{p+s}(x', y', T_{n-1}(x, y), \theta_{x,y}) = \quad (21)$$
$$K_{p+s}(x', y', T_{n-1}(x, y) + dt, \theta_{x,y}) - K_{p+s}(x', y', T_{n-1}(x, y), \theta_{x,y})$$

However, in Expression (19), α is an update coefficient which is a parameter indicating the update speed of the body thickness. As an example of a method for calculating a differential value portion of Kp+s shown in Expression (20), for example, a value change when a very small value dt is added to Tn−1(x, y) can be calculated by Expression (21) and can be used as the value of Kp+s in the Expression (20). In Expressions (11) to (21), the same components are denoted by the same reference numerals and the description thereof will not be repeated. Any optimization method can be applied as long as it can minimize the error value $V_{error}$ indicating the difference between the radiographic image and the estimated image Im. For example, a simplex method, the steepest descent method, or a conjugate gradient method can be used.

When the corrected body thickness distribution Tn is acquired, the body thickness distribution determination unit 64 increases the value of n by 1 to update the value of n (n=n+1) and the virtual model acquisition unit 61 acquires the corrected body thickness distribution Tn (Step ST31). Then, the estimated image generation unit 62 and the body thickness distribution determination unit 64 perform the process from Step ST31 to Step ST33 for the acquired body thickness distribution Tn, using the same method as described above. Then, similarly, the process of correcting the body thickness distribution Tn (Step ST34), the process of acquiring the virtual model K having the corrected body thickness distribution Tn (Step ST31), the process of generating a new estimated image Im using the body thickness distribution Tn (Step ST32), and the process of determining whether the difference between a newly generated estimated image Im and the radiographic image satisfies the end conditions (Step ST33) are repeatedly performed until the error value $V_{error}$ indicating the difference between the radiographic image and the estimated image Im satisfies the end conditions.

On the other hand, in a case in which it is determined that the error value $V_{error}$ satisfies the end conditions (Step ST33: Yes), the body thickness distribution determination unit 64 determines the body thickness distribution Tn which is used for the error value $V_{error}$ when the end conditions are satisfied as the body thickness distribution Tk of the radiographic image and ends the body thickness estimation process (Step ST35).

Returning to FIG. 11, following the body thickness estimation process, a scattered radiation removal process is performed using the estimated body thickness distribution (Step ST23). Since the scattered radiation removal process is the same as the process from Step ST2 to Step ST8 in the flowchart illustrated in FIG. 8, the detailed description thereof will not be repeated in this embodiment. Here, the body thickness distribution T(x, y) in Expressions (1) and (2) is calculated by the same method as that in the first embodiment. A processed radiographic image subjected to the scattered radiation removal process is displayed on the display unit 3 (Step ST24). In the second embodiment, a confirmation screen differs from the confirmation screen illustrated in FIG. 6 in that the body type selection region 52 is omitted and only the image display region 51, the confirmation completion button 53, the correction button 54, and the re-imaging button 55 are displayed.

Then, the control unit 41 determines whether a body type correction instruction has been received (Step ST25). When the determination result in Step ST25 is "Yes", the correction information acquisition unit 45 acquires the body type of the subject M as the correction information on the basis of the body thickness distribution Tk(x, y) estimated by the body thickness estimation unit 47 (Step ST26) and changes the imaging conditions on the basis of the correction information (Step ST27). A table in which various body thickness distributions are associated with body types (fat, slightly fat, normal, slightly thin, and thin) is stored in the storage unit 46. The correction information acquisition unit 45 acquires the body type of the subject M as the correction information with reference to the table and acquires the changed imaging conditions with reference to the table LUT2.

Then, returning to Step ST22, the body thickness estimation process in Step ST22 and the scattered radiation removal process in Step ST23 are performed on the basis of the changed imaging conditions. In the body thickness estimation process, kernels Ks(x, y, Tn(x', y'), θx', y') and Kp+s(x, y, Tn−1(x', y'), θx', y') are calculated on the basis of the changed imaging conditions and a new body thickness distribution Tk is estimated. In the scattered radiation removal process, a kernel Sσ(T(x, y)) is calculated on the basis of the changed imaging conditions and a new scattered radiation content distribution S(x, y) is calculated, using the above-mentioned Expressions (1) to (3). In addition, a new processed radiographic image I'(x, y) is acquired, using Expressions (4) and (5).

When the determination result in Step ST25 is "No", the control unit 41 determines whether the re-imaging button 55 has been selected (Step ST28). When the determination result in Step ST28 is "Yes", the control unit 41 ends the process for re-imaging. When the determination result in Step ST28 is "No", the control unit 41 determines whether the confirmation completion button 53 has been selected (Step ST29). When the determination result in Step ST29 is "No", the process returns to Step ST25. On the other hand, when the determination result in Step ST29 is "Yes", the process ends. The processed radiographic image is transmitted to the center console PC 5 and is then stored therein.

As such, in the second embodiment, the body thickness distribution of the subject is estimated. In a case in which a correction instruction is issued, a process which changes the imaging conditions, using the body thickness distribution as the correction information, and removes a scattered component on the basis of the changed imaging conditions is performed. Therefore, it is possible to appropriately remove a scattered component according to the estimated body thickness distribution and thus to acquire a high-quality radiographic image.

In addition, since the body thickness distribution is estimated on the basis of the changed imaging conditions, it is possible to appropriately estimate the body thickness distribution.

In the second embodiment, in a case in which a correction instruction is issued, both the body thickness estimation process and the scattered radiation removal process are performed on the basis of the changed imaging conditions. However, only the body thickness estimation process may be performed on the basis of the changed imaging conditions.

Figure 16:
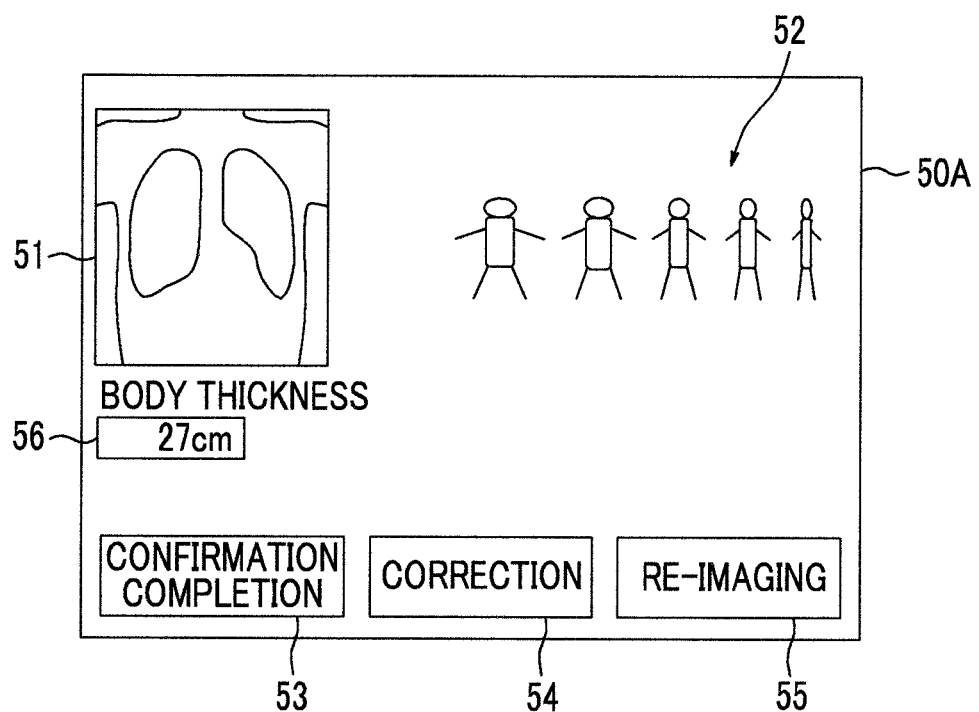
FIG. 16 is a diagram illustrating another example of the confirmation screen.

In the second embodiment, the estimated body thickness distribution may be used as auxiliary information for selecting the body type on the confirmation screen. FIG. 16 is a diagram illustrating another example of the confirmation screen. As illustrated in FIG. 16, in addition to the image display region 51, the body type selection region 52, the confirmation completion button 53, the correction button 54, and the re-imaging button 55, a body thickness display region 56 is displayed on the confirmation screen 50A. The representative value of the body thickness distribution Tk(x, y) estimated by the body thickness estimation unit 47 is displayed in the body thickness display region. In FIG. 16, 27 cm is displayed. In addition, as the representative value, for example, the following may be used: the maximum value, mean, and median of the body thickness distribution Tk(x, y); a weighted mean except for an outlier in the body thickness distribution Tk(x, y); and a body thickness at the center of a radiographic image. In addition, as the representative value of the body thickness, a body thickness distribution color map in which the position of each pixel in a radiographic image and a body thickness are associated with each other may be displayed.

As such, since the representative value of the body thickness distribution is displayed, it is possible to easily select a body type in the body type selection region 52. Therefore, it is possible to reduce a burden on the operator when the operator inputs a correction instruction.

In some cases, an implant, such as metal or silicon, which is inserted into the body by a surgical operation is included in a radiographic image. In this case, since an implant region included in the radiographic image has a higher brightness than tissues in the subject M, the body thickness distribution Tk(x, y) in the implant region is less likely to be accurate. For this reason, when the correction information acquisition unit 45 calculates the representative value of the body thickness, it is preferable that the implant region is excluded.

In a case in which the maximum value of the body thickness distribution is used as the representative value, for example, a pixel position where the body thickness distribution has the maximum value on the radiographic image displayed on the image display region 51 may be marked to notify the operator of the maximum value of the body thickness distribution.

In the first and second embodiments, it is preferable that the radiographic image has a pixel value which is proportional to an incident dose on the radiation detector, the scattered radiation removal process is performed in a space that is linear with respect to a radiation dose, and logarithmic conversion is performed to convert the space into a logarithmically linear space that is proportional to the human vision.

In the first and second embodiments, the characteristic acquisition unit 42 acquires the scattered radiation transmittance Ts and the primary radiation transmittance Tp as the virtual grid characteristics. However, the characteristic acquisition unit 42 may acquire only the scattered radiation transmittance Ts or the primary radiation transmittance Tp.

In the first and second embodiment, the operator selects an icon corresponding to the body type of the subject M on the confirmation screen to input information about the desired body type. However, instead of the selection of the icon, a slide bar may be used to input information about the body type. In this case, the slide bar can be used to select any position between the fat body type to the thin body type and the operator moves the position of the slide bar according to the desired body type to select the correction button 54. Then, the correction information acquisition unit 45 acquires information about the body type corresponding to the position of the slide bar as the correction information. In addition, a value indicating the body type may be input. In this case, for example, values corresponding to the body types may be defined in advance in such a manner that 50 is given to a standard body type, 10 is given to the thinnest body type, and 90 is given to the fattest body type and the value corresponding to the body type of the subject M may be input on the confirmation screen.

In some cases, a radiographic image is captured, without using a scattered radiation removal grid, according to the part of which the image is to be captured. It is not preferable to perform the scattered radiation removal process according to the first and second embodiments for the acquired radiographic image of the part. Therefore, it is preferable that the scattered radiation removal process according to this embodiment is turned on or off according to the part of which the image is to be captured. Information about the part of which the image is to be captured may be acquired from the input of the operator or may be automatically acquired from an imaging request which is input to a known console PC (not illustrated) for controlling an imaging flow. Alternatively, information which is attached to the radiographic image by the system after imaging and is then stored may be used. In a case in which it is difficult to acquire the above-mentioned information, a part recognition process may be performed for the radiographic image to acquire the information. In this case, a table in which information indicating whether to turn on or off the process is associated with each part may be stored in the storage unit 46 and the process may be turned on or off with reference to the table.

In the first and second embodiments, both the processed radiographic image and the radiographic image before the process are displayed. However, of the two radiographic images, the radiographic image to be used for diagnosis may be selected.

For the mAs value among the imaging conditions to be changed, the radiographic image of an acrylic model having a known thickness may be captured together with the radiographic image of the subject and the mAs value may be acquired on the basis of the concentration of the acrylic model in the acquired radiographic image. In this case, a table in which the concentration of the acrylic model is associated with the mAs value may be stored in the storage unit 46 and the mAs value may be acquired on the basis of the concentration of the acrylic model, with reference to the table. In a case in which a void region that is obtained by the direct emission of X-rays to the radiation detector 20 is included in the radiographic image, the mAs value may be acquired on the basis of the concentration of the void region. In this case, a table in which the concentration of the void region is associated with the mAs value may be stored in the storage unit 46 and the mAs value may be acquired on the basis of the concentration of the void region, with reference to the table.

There is a case in which time-dependent comparison and observation is performed, using the previous radiographic images, in order to diagnose the healing state or progress state of a disease. In a case in which a radiographic image (referred to as a first radiographic image) which is captured without using a scattered radiation removal grid is compared with a radiographic image (referred to as a second radiographic image) which is captured using the scattered radiation removal grid, it is preferable to correct the conditions of the scattered radiation removal process according to this embodiment, on the basis of the processing conditions when a process of removing a stripe pattern caused by the grid is performed for the first radiographic image such that the first and second radiographic images have the same image quality.

In the above-described embodiments, the scattered radiation removal process is performed, using the radiographic image acquired by the system which captures the radiographic image of the subject using the radiation detector 20. However, the invention can be applied to the structures disclosed in JP1996-266529A (JP-H08-266529A) and JP1997-24039A (JP-H09-24039A) in which the radiographic image information of the subject is stored and recorded on a storage phosphor sheet as a radiation detector and the radiographic image is photoelectrically read and acquired from the storage phosphor sheet and is then used.

What is claimed is:

1. A radiographic image processing device comprising:
   an image acquisition unit for acquiring a radiographic image which is captured by irradiating a subject with radiation;
   a scattered radiation removal processing unit for performing a process of removing a scattered component included in the radiation that is transmitted through the subject during imaging from the radiographic image, using at least imaging conditions; and
   a correction information acquisition unit for acquiring correction information for correcting a degree of removal of the scattered component and changing the imaging conditions on the basis of the correction information, in response to an instruction to correct the radiographic image subjected to the scattered radiation removal process,
   wherein the scattered radiation removal unit performs the process of removing the scattered component from the radiographic image on the basis of the changed imaging conditions.

2. The radiographic image processing device according to claim 1,
   wherein the correction information is information related to a body type of the subject.

3. The radiographic image processing device according to claim 1, further comprising:
   a body thickness distribution estimation unit for estimating a body thickness distribution of the subject on the basis of the radiographic image and the imaging conditions,
   wherein the correction information acquisition unit acquires information related to the body thickness distribution as the correction information and changes the imaging conditions on the basis of the correction information, in response to the correction instruction, and
   the body thickness distribution estimation unit estimates the body thickness distribution on the basis of the changed imaging conditions.

4. The radiographic image processing device according to claim 3,
   wherein the scattered radiation removal processing unit performs the process of removing the scattered component on the basis of the changed imaging conditions and the body thickness distribution.

5. The radiographic image processing device according to claim 3,
   wherein the correction information acquisition unit acquires information related to a body type of the subject on the basis of the body thickness distribution, displays the information related to the body type, receives an input of the correction information, and acquires the correction information.

6. The radiographic image processing device according to claim 5,
   wherein the correction information acquisition unit detects an implant region from the radiographic image and acquires the information related to the body type on the basis of the body thickness distribution in a region other than the implant region in the radiographic image.

7. A radiographic image processing method comprising:
   acquiring a radiographic image which is captured by irradiating a subject with radiation;
   performing a process of removing a scattered component included in the radiation that is transmitted through the subject during imaging from the radiographic image, using at least imaging conditions;
   acquiring correction information for correcting a degree of removal of the scattered component and changing the imaging conditions on the basis of the correction information, in response to an instruction to correct the radiographic image subjected to the scattered radiation removal process; and
   performing the process of removing the scattered component from the radiographic image on the basis of the changed imaging conditions.

8. A non-transitory recording medium having stored therein a radiographic image processing program that causes a computer to perform:
   a step of acquiring a radiographic image which is captured by irradiating a subject with radiation;
   a step of performing a process of removing a scattered component included in the radiation that is transmitted through the subject during imaging from the radiographic image, using at least imaging conditions;
   a step of acquiring correction information for correcting a degree of removal of the scattered component and changing the imaging conditions on the basis of the correction information, in response to an instruction to correct the radiographic image subjected to the scattered radiation removal process, and
   a step of performing the process of removing the scattered component from the radiographic image on the basis of the changed imaging conditions.

* * * * *